United States Patent [19]

Sirosita et al.

[11] Patent Number: 4,986,989
[45] Date of Patent: Jan. 22, 1991

[54] ZEOLITE FUNGICIDE

[75] Inventors: Masao Sirosita, Nishinomiya; Masato Mizutani, Toyonaka; Shigeko Kimura, Otsu, all of Japan; Yukio Oguri, Chaville, France; Masaru Kitamura; Youichi Umada, both of Takatsuki, Japan; Hiroshi Sato, Niihama, Japan

[73] Assignee: Sumitomo Chemical Company, Limited, Osaka, Japan

[21] Appl. No.: 236,715

[22] Filed: Aug. 26, 1988

[30] Foreign Application Priority Data

Sep. 4, 1987 [JP] Japan .............................. 62-222293

[51] Int. Cl.$^5$ ............................................ A01N 59/20
[52] U.S. Cl. .................................................... 424/635
[58] Field of Search ......................................... 424/635

[56] References Cited

U.S. PATENT DOCUMENTS 3,649,177  3/1972  Roebeck ................................ 23/111
4,525,410  6/1985  Hagiwara et al. ................... 424/619

FOREIGN PATENT DOCUMENTS

AUB23546  1/1986  Australia .
2010214   3/1984  European Pat. Off. .

OTHER PUBLICATIONS

Central Patents Index, Basic Abstracts Journal, section C, week 8448, Jan. 30, '85, No. 84-298611/48, Derwent Pub. Ltd., London, GB; JP-A-59 186 908 (Nippon Chem. Ind. KK).
Central Patents Index, Basic Abstracts Journal, Sec. C, week 8543, Dec. 18, 1985, No. 85-267424/43, Derwent Publ., Ltd., London, GB; & JP-A-60 181 002 (Shinnanen New Ceramics) 14-09-1985.

Primary Examiner—Allen J. Robinson
Attorney, Agent, or Firm—Stevens, Davis, Miller & Mosher

[57] ABSTRACT

A novel agricultural and horticultural fungicide is disclosed. It contains as an active ingredient at least one crystalline zeolite selected from the group consisting of faujasite group, chabazite group and phillipsite group represented by the formula, $$aCuO.(1-a)M_2O.Al_2O_3.bSiO_2.cH_2O$$

wherein M represents a sodium and/or potassium atom, and a, b and c fall in the following ranges, $$0 < a \leq 1,\ 3 < b \leq 12,\ 0 \leq c \leq 20.$$

The fungicide shows a high activity against various diseases of fruits trees, vegetables, etc. and can be safely applied to crops.

4 Claims, No Drawings

ZEOLITE FUNGICIDE

The present invention relates to an agricultural and horticultural fungicide containing as an active ingredient at least one crystalline zeolite selected from the group consisting of faujasite group, chabazite group and phillipsite group represented by the formula (I) (hereinafter referred to as the present substance), $$aCuO \cdot (1-a)M_2O \cdot Al_2O_3 \cdot bSiO_2 \cdot cH_2O \qquad (I)$$

wherein M represents a sodium and/or potassium atom, and a, b and c fall in the following ranges, $$0 < a \leq 1,\ 3 < b \leq 12,\ 0 \leq c \leq 20.$$

Among the present substances, what is particularly superior in terms of the controlling activity is at least one crystalline zeolite selected from the group consisting of faujasite group and phillipsite group represented by the formula, $$aCuO \cdot (1-a)M_2O \cdot Al_2O_3 \cdot bSiO_2 \cdot cH_2O$$

wherein M represents a sodium and/or potassium atom, and a, b and c fall in the following ranges, $$0 < a \leq 1,\ 3.5 < b < 8,\ 0 \leq c \leq 20.$$

Hitherto, as the fungicide for fruit trees, vegetables, etc., inorganic copper-containing chemicals such as a Bordeaux mixture, etc. have been used.

However, these known fungicides are not satisfactory because they show efficacy only against narrow range of deseases and the phytotoxicity to crops limits the range of the application. Consequently, developing high-performance chemicals which give little phytotoxicity and are effective at a low dosage rate has been desired.

In recognition of the situation, the present inventors have extensively studied to find chemicals which have an excellent activity against various diseases of fruit trees, vegetables, etc. and can safely be applied to crops, and as a result, have surprisingly found that the present substance has an excellent fungicidal activity and yet shows no problematic phytotoxicity. The present inventors thus attained to the present invention.

JP-A-59-186908 discloses that a product obtained by copper ion exchange of aluminosilicate can be used as an agricultural and horticultural fungicide. In reality, however, the copper-containing aluminosilicate disclosed in the above literature does not have a strong fungicidal activity per copper content and it cannot compensate the defect of the conventional inorganic copper-containing chemicals.

The present inventors have extensively studied to develop a chemical having sufficiently high fungicidal activity per copper content enough to be highly effective at a low dosage rate of copper, and as a result, have found that the crystalline zeolite represented by the foregoing formula (I) has an extremely high activity per copper content.

Comparing the activity per copper content of the existing inorganic copper-containing chemicals with that of the present substance shows that, although depending upon diseases to be controlled, the present substance has an activity more than 10 times as high as the existing chemicals, as described in the following examples about many diseases. Such a marked development in the activity per copper content is epoch-making, and highly active copper-containing chemicals such as the present substance have not been known in spite of studies on copper fungicides for more than the past 100 years.

A great improvement in the activity per copper content results in various advantages in controlling crop diseases. That is, since the agricultural and horticultural fungicide of the present invention exhibits an excellent activity against various plant diseases, it has a number of advantages as follows:

Its dosage rate can be reduced because the phytotoxicity to crops can be markedly improved. It can be satisfactorily applied to various crops to which the existing metal-containing fungicides such as a Bordeaux mixture, etc. cannot be applied. And because of a great improvement in its activity per copper content, it has an advantage that it can be applied without increasing a residual copper content to a field containing a large amount of residual copper in the soil.

The copper content of the present substance can be determined optionally, but preferably, it is at most the amount of copper atoms when all of $M_2$ in the foregoing formula are substituted by copper atoms.

The present substance can be obtained by a known method. An example thereof is a method comprising adding an aqueous sodium or potassium aluminate solution and an aqueous sodium or potassium silicate solution in a prescribed concentration ratio to an aqueous caustic soda or caustic potash solution, carrying out hydrothermal synthesis to produce zeolite, the precursor of the present substance, followed by ion-exchanging the zeolite with a water-soluble copper salt in water or an alcohol. The water-soluble copper salt used in this reaction includes for example mineral acid salts of copper such as cupric chloride, cupric sulfate, cupric nitrate, etc. Further, organic acid salts (e.g. cupric acetate, cupric formate), ammonia-copper complex salts, etc. may also be used.

Because the present substance exhibits an excellent effect against plant diseases, it can be used in various applications as an active ingredient for agricultural and horticultural fungicides.

As examples of plant diseases which can be controlled by the present substance, there may be mentioned the following diseases: Bacterial soft rot of various vegetables (*Erwinia carotovora*), bacterial wilt of solanaceous plants (*Pseudomonas solanacearum*), angular leaf spot of cucumber (*Pseudomonas lachrymans*), bacterial leaf spot of vegetables (*Pseudomonas syringae pv. maculicola*), black rot of vegetables (*Xanthomonas campestris*), Crown gall of vegetables (*Agrobacterium tumefaciens*), bacterial canker of tomato (*Corynebacterium michiganense*), bacterial grain rot of rice (*Pseudomonas glumae*), wild fire of tobacco (*Pseudomonas tabaci*), canker of citrus (*Xanthomonas campestris pv. citri*), bacterial leaf blight of rice (*Xanthomonas oryzae*), downy mildew of vegetables and Japanese radish (*Peronospora brassicae*), downy mildew of spinach (*Peronospora spinaciae*), downy mildew of tobacco (*Peronospora tabacina*), downy mildew of cucumber (*Pseudoperonospora cubensis*), downy mildew of grape (*Plasmopara viticola*), downy mildew of dropwort (*Plasmopara nivea*), late blight of apple, strawberry and ginseng (*Phytophthora cactorum*), phytophthora rot of tomato and cucumber (*Phytophthora capsici*), late blight of pineapple (*Phytophthora cinnamomi*), late blight of potato, tomato and eggplant (*Phytophthora infestans*), late blight of tobacco, broad bean and Welsh onion (*Phytophthora nicotianae var. nicotianae*), damping-off of spinach (*Pythium* sp.), damping-off of cucumber (*Pythium aphanidermatum*), browning root rot of wheat (*Pythium* sp.), damping-off of tobacco (*Pythium debaryanum*), pythium rot of soybean (*Pythium aphanidermatum, P. debaryanum, P. irregulare, P. myriotylum, P. ultimum*), blast or rice (*Pyricularia oryzae*), helminthosporium leaf spot of rice (*Cochliobolus miyabeanus*), scab of apple (*Venturia inaequalis*), canker of apple (*Valsa mali*), alternaria leaf spot of apple (*Alternaria mali*), black spot of pear (*Alternaria kikuchiana*), scab of pear (*Venturia nashicola*), melanose of citrus (*Diaporthe citri*), anthracnose of Japanese persimmon (*Gloeosporium kaki*), leaf spot of Japanese persimmon (*Cercospora kaki, Mycosphaerella nawae*), ripe rot of grape (*Glomerella cingulata*), gray mold of grape (*Botrytis cinerea*), speckled leaf blotch of wheat (*Septoria tritici*), glume blotch of wheat (*Leptosphaeria nodorum*), anthracnose of melons (*Colletotrichum lagenarium*), gummy stem blight of melons (*Mycosphaerella melonis*), early blight of tomato (*Alternaria solani*), brown spot of tobacco (*Alternaria longipes*), anthracnose of tobacco (*Collectotrichum tabacum*), cercospora leaf spot of beet (*Cercospora beticola*), early blight of potato (*Alternaria solani*), brown leaf spot of peanut (*Cercospora arachidicola*), septoria brown spot of soybean (*Septoria glycines*), pod and stem blight of soybean (*Diaporthe phaseololum*), anthracnose of soybean (Colletotrichum sp.), purple stain of soybean (*Cercospora kikuchii*), etc.

The present substance can be used as an agricultural and horticultural fungicide in plow fields, paddy fields, orchards, tea gradens, pastures, turfs, etc. Also, the present substance can be used in mixture with other fungicides, insecticides, acaricides, nematocides, herbicides, plant growth regulators and fertilizers.

When the present substance is used as an active ingredient for fungicides, it may be used as it is without adding any other ingredients. Usually, however, it is formulated before use into granules, wettable powders, suspension formulations, dusts, etc. by mixing with solid carriers, liquid carriers, surface active agents and other auxiliaries for formulation. The content of the present substance in these preparations is from 0.1 to 99.9%, preferably from 1 to 99%.

The solid carriers include fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide, etc. The liquid carriers include water.

The surface active agents used for emulsification, dispersion, wetting, etc. include anionic surface active agents such as the salt of alkyl sulfates, alkyl(aryl)sulfonates, dialkyl sulfosuccinates, the salt of polyoxyethylene alkylaryl ether phosphoric acid esters, naphthalenesulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation include lignosulfonates, alginates, polyvinyl alcohol, gum arabic, CMC (carboxymethyl cellulose), PAP (isopropyl acid phosphate), etc.

The application method for the agricultural and horticultural fungicide of the present invention includes for example foliage application, soil treatment, seed disinfection, etc., but usually, the present fungicide may be used by any method used by those skilled in the art.

When the present substance is used as an active ingredient for agricultural and horticultural fungicides, the dosage rate of the active ingredient varies with crops to be protected, diseases to be controlled, degree of outbreak of diseases, preparation forms, application methods, application time, weather conditions, copper contents, etc., but it is usually from 0.3 to 600 g/are, preferably from 0.3 to 300 g/are. When the wettable powders, suspension formulations, etc. are applied in dilution with water, the application concentration of the present substance is from 0.015 to 1.5%, preferably from 0.03 to 0.6%. The dusts, granules, etc. are applied as they are without dilution.

The following examples serve to give specific illustrations of the practice of the present invention, but they are not intended in any way to limit the scope of the present invention.

First, formulation examples are shown. In the examples, parts are by weight.

FORMULATION EXAMPLE 1

Thoroughly pulverizing and mixing 50 parts of the present substance, 3 parts of calcium lignosulfonate, 2 parts of sodium lauryl sulfate and 45 parts of synthetic hydrated silicon dioxide gives a wettable powder.

FORMULATION EXAMPLE 2

Thoroughly pulverizing and mixing 95 parts of the present substance, 3 parts of calcium lignosulfonate, 2 parts of sodium lauryl sulfate gives a wettable powder.

FORMULATION EXAMPLE 3

Mixing and wet-pulverizing 50 parts of the present substance, 3 parts of polyoxyethylene sorbitan monooleate, 3 parts of CMC and 44 parts of water so as to the particle size of the active ingredient is reduced to 5 microns or less gives a suspension formulation.

FORMULATION EXAMPLE 4

Thoroughly pulverizing and mixing 5 parts of the present substance, 85 parts of kaolin clay and 10 parts of talc gives a dust.

FORMULATION EXAMPLE 5

Thoroughly pulverizing and mixing 20 parts of the present substance, 1 part of synthetic hydrated silicon dioxide, 2 parts of calcium lignosulfonate, 30 parts of bentonite and 48 parts of kaolin clay followed by well kneading with water, granulating and drying gives a granule.

Next, the usefulness of the present substance as an agricultural and horticultural fungicide are shown with reference to the following test examples.

In the test examples, test substances were prepared by the following operations.

PRESENT SUBSTANCE (1)

Fifteen grams of sodium aluminate containing 26.3 wt.% of $Na_2O$, 43.2 wt.% of $Al_2O_3$ and 30.5 wt.% of $H_2O$ and 63.85 g of sodium hydroxide containing 77.5 wt.% of $Na_2O$ were dissolved in 276.04 g of distilled water. This solution was added to 352.43 g of an aqueous colloidal silica sol containing 0.4 wt.% of $Na_2O$ and 30.5 wt.% of $SiO_2$ with stirring. The substance thus obtained has the formula, $13.9Na_2O \cdot Al_2O_3 \cdot 28.2SiO_2 \cdot 470.9H_2O$.

Then, the reactor was closed tightly, the substance charged therein was stirred firstly at room temperature for 24 hours and then at 100° C. for 24 hours. Precipitated powdery crystals were collected by filtration under reduced pressure, washed with distilled water until the pH of the washings became from about 8 to about 9 and dried at 120° C. for 16 hours.

To 5 g of these crystals were added 118 ml of a 0.04 M aqueous copper sulfate solution. Then, the pH of the system was adjusted to 4.2 with 10% sulfuric acid and ion exchange was carried out with stirring at 70° C. for 3 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was crystalline zeolite belonging to faujasite group. The elementary analysis showed that the atomic ratio of Si to Al was 2.68 and the copper content was 4.6 wt.%. This substance has the formula,

$0.48CuO \cdot 0.52Na_2O \cdot Al_2O_3 \cdot 5.36SiO_2 \cdot 9.25H_2O.$

PRESENT SUBSTANCE (2)

Twenty-five grams of sodium aluminate containing 26.3 wt.% of $Na_2O$, 43.2 wt.% of $Al_2O_3$ and 30.5 wt.% of $H_2O$ and 52.4 g of sodium hydroxide containing 77.5 wt.% of $Na_2O$ were dissolved in 612.1 g of distilled water. This solution was added to 379.9 g of an aqueous sodium silicate solution containing 9.2 wt.% of $Na_2O$ and 29.0 wt.% of $SiO_2$ with stirring. The substance thus obtained has the formula, $12.5Na_2O \cdot Al_2O_3 \cdot 17.3SiO_2 \cdot 454.5H_2O.$ Then, the reactor was closed tightly, the substance charged therein was stirred at 100° C. for 48 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was crystalline zeolite belonging to phillipsite group. The elementary analysis showed that the atomic ratio of Si to Al was 1.91 and the copper content was 3.8 wt.%. The electron microscopic measurement showed that the average particle diameter was 2.0 μm. This substance has the formula, $0.32CuO \cdot 0.68Na_2O \cdot Al_2O_3 \cdot 3.82SiO_2 \cdot 7.79H_2O.$

PRESENT SUBSTANCE (3)

Fifteen grams of sodium aluminate containing 26.3 wt.% of $Na_2O$, 43.2 wt.% of $Al_2O_3$ and 30.5 wt.% of $H_2O$ and 65.74 g of sodium hydroxide containing 77.5 wt.% of $Na_2O$ were dissolved in 519.09 g of distilled water. To this solution were added 107.49 g of $SiO_2$ (Aerosil) with stirring. The substance thus obtained has the formula, $13.9Na_2O \cdot Al_2O_3 \cdot 28.2SiO_2 \cdot 470.9H_2O.$ Then, the reactor was closed tightly, and the substance charged therein was stirred firstly at room temperature for 24 hours and then at 100° C. for 24 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was crystalline zeolite belonging to phillipsite group. The elementary analysis showed that the atomic ratio of Si to Al was 2.39 and the copper content was 3.2 wt.%. This substance has the formula, $0.32CuO \cdot 0.68Na_2O \cdot Al_2O_3 \cdot 4.78SiO_2 \cdot 9.48H_2O.$

PRESENT SUBSTANCE (4)

Fifteen grams of sodium aluminate containing 26.3 wt.% of $Na_2O$, 43.2 wt.% of $Al_2O_3$ and 30.5 wt.% of $H_2O$ and 63.85 g of sodium hydroxide containing 77.5 wt.% of $Na_2O$ were dissolved in 276.04 g of distilled water. This solution was added to 352.43 g of an aqueous colloidal silica sol containing 0.4 wt.% of $Na_2O$ and 30.5 wt.% of $SiO_2$ with stirring. The substance thus obtained has the formula, $13.9Na_2O \cdot Al_2O_3 \cdot 28.2SiO_2 \cdot 470.9H_2O.$ Then, the reactor was closed tightly, the substance charged therein was stirred firstly at room temperature for 24 hours and then at 100° C. for 24 hours. Thereafter, the temperature was lowered again to room temperature, the stirring was carried out at 100° C. for another 48 hours.

Next, precipitated powdery crystals were collected by filtration under reduced pressure, washed with distilled water until the pH of the washings became from about 8 to about 9 and dried at 120° C. for 16 hours.

Thereafter, copper ion exchange was carried out in the same manner as in the preparation of the present substance (1).

The X-ray diffractometry demonstrated that the powdery substance thus obtained was crystalline zeolite belonging to phillipsite group. The elementary analysis showed that the atomic ratio of Si to Al was 2.59 and the copper content was 3.4 wt.%. This substance has the formula, $0.35CuO \cdot 0.65Na_2O \cdot Al_2O_3 \cdot 5.18SiO_2 \cdot 9.79H_2O.$

PRESENT SUBSTANCE (5)

Fifteen grams of sodium aluminate containing 26.3 wt.% of $Na_2O$, 43.2 wt.% of $Al_2O_3$ and 30.5 wt.% of $H_2O$ and 63.85 g of sodium hydroxide containing 77.5 wt.% of $Na_2O$ were dissolved in 276.04 g of distilled water. This solution was added to 352.43 g of an aqueous colloidal silica sol containing 0.4 wt.% of $Na_2O$ and 30.5 wt.% of $SiO_2$ with stirring. The substance thus obtained has the formula, $13.9Na_2O \cdot Al_2O_3 \cdot 28.2SiO_2 \cdot 470.9H_2O.$ Then, the reactor was closed tightly, and the substance charged therein was stirred firstly at room temperature for 24 hours and then at 100° C. for 18 hours. Precipitated powdery crystals were collected by filtration under reduced pressure, washed with distilled water until the pH of the washings became from about 8 to about 9 and dried at 120° C for 16 hours.

Next, copper ion exchange was carried out in the same manner as in the preparation of the present substance (1).

The X-ray diffractometry demonstrated that the powdery substance thus obtained was crystalline zeolite belonging to faujasite group. The elementary analysis showed that the atomic ratio of Si to Al was 2.58 and the copper content was 4.7 wt.% This substance has the formula, $0.48CuO \cdot 0.52Na_2O \cdot Al_2O_3 \cdot 5.16SiO_2 \cdot 8.93H_2O$.

PRESENT SUBSTANCE (6)

Fifteen grams of sodium aluminate containing 26.3 wt.% of $Na_2O$, 43.2 wt.% of $Al_2O_3$ and 30.5 wt.% of $H_2O$ and 141.63 g of sodium hydroxide containing 77.5 wt.% of $Na_2O$ were dissolved in 68.09 g of distilled water. This solution was added to 128.73 g of an aqueous colloidal silica sol containing 0.4 wt.% of $Na_2O$ and 30.5 wt.% of $SiO_2$ with stirring. The substance thus obtained has the formula, $29.0Na_2O \cdot Al_2O_3 \cdot 10.3SiO_2 \cdot 126.2H_2O$.

Then, the reactor was closed tightly, and the substance charged therein was stirred firstly at room temperature for 24 hours and then at 100° C. for 130 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was crystalline zeolite belonging to faujasite group. The elementary analysis showed that the atomic ratio of Si to Al was 2.76 and the copper content was 5.4 wt.%. This substance has the formula, $0.57CuO \cdot 0.43Na_2O \cdot Al_2O_3 \cdot 5.52SiO_2 \cdot 8.87H_2O$.

PRESENT SUBSTANCE (7)

Fifteen grams of sodium aluminate containing 26.3 wt.% of $Na_2O$, 43.2 wt.% of $Al_2O_3$ and 30.5 wt.% of $H_2O$ and 63.85 g of sodium hydroxide containing 77.5 wt.% of $Na_2O$ were dissolved in 276.04 g of distilled water. This solution was added to 352.43 g of an aqueous colloidal silica sol containing 0.4 wt.% of $Na_2O$ and 30.5 wt.% of $SiO_2$ with stirring. The substance thus obtained has the formula, $13.9Na_2O \cdot Al_2O_3 \cdot 28.2SiO_2 \cdot 470.9H_2O$.

Then, the reactor was closed tightly, and the substance charged therein was stirred firstly at room temperature for 24 hours and then at 100° C. for 65 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was crystalline zeolite belonging to faujasite group. The elementary analysis showed that the atomic ratio of Si to Al was 2.35 and the copper content was 5.1 wt.%. The electron microscopic measurement showed that the average particle diameter was 1.0 μm. This substance has the formula, $0.48CuO \cdot 0.52Na_2O \cdot Al_2O_3 \cdot 4.70SiO_2 \cdot 8.15H_2O$.

PRESENT SUBSTANCE (8)

Crystalline zeolite before the copper ion exchange was obtained in the same manner as in the preparation of the present substance (5). Then, 2070 ml of a 0.3 M aqueous copper sulfate solution was added to 90 g of zeolite thus obtained, the pH of the system was adjusted to 4.2 with 10% sulfuric acid and ion exchange was carried out with stirring at 70° C. for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was crystalline zeolite belonging to faujasite group. The elementary analysis showed that the atomic ratio of Si to Al was 2.58 and the copper content was 7.8 wt.%. The electron microscopic measurement showed that the average particle diameter was 1.5 μm. This substance has the formula, $0.78CuO \cdot 0.22Na_2O \cdot Al_2O_3 \cdot 5.16SiO_2 \cdot 8.09H_2O$.

PRESENT SUBSTANCE (9)

Fifteen grams of sodium aluminate containing 26.3 wt.% of $Na_2O$, 43.2 wt.% of $Al_2O_3$ and 30.5 wt.% of $H_2O$ and 63.85 g of sodium hydroxide containing 77.5 wt.% of $Na_2O$ were dissolved in 276.04 g of distilled water. This solution was added to 352.43 g of an aqueous colloidal silica sol containing 0.4 wt.% of $Na_2O$ and 30.5 wt.% of $SiO_2$ with stirring. The substance thus obtained has the formula, $13.9Na_2O \cdot Al_2O_3 \cdot 28.2SiO_2 \cdot 470.9H_2O$.

Then, the reactor was closed tightly, and the substance charged therein was stirred firstly at room temperature for 24 hours and then at 80° C. for 168 hours. Precipitated powdery crystals were collected by filtration under reduced pressure, washed with distilled water until the pH of the washings became from about 8 to about 9 and dried at 120° C. for 16 hours.

Next, to 5 g of these crystals were added 100 ml of a 0.048 M aqueous copper sulfate solution, the pH of the system was adjusted to 4.2 with 10% hydrochloric acid and ion exchange was carried out with stirring at 75° C. for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was crystalline zeolite belonging to faujasite group. The elementary analysis showed that the atomic ratio of Si to Al was 2.47 and the copper content was 7.0 wt.%. Electron microscopic measurement showed that the average particle diameter was 0.5 μm. This substance has the formula, $0.68CuO \cdot 0.32Na_2O \cdot Al_2O_3 \cdot 4.94SiO_2 \cdot 8.02H_2O$.

PRESENT SUBSTANCE (10)

Fifteen grams of sodium aluminate containing 26.3 wt.% of $Na_2O$, 43.2 wt.% of $Al_2O_3$ and 30.5 wt.% of $H_2O$, 20.89 g of sodium hydroxide containing 77.5 wt.% of $Na_2O$ and 39.71 g of potassium hydroxide containing 84.0 wt.% of $K_2O$ were dissolved in 266.42 g of distilled water. This solution was added to 354.53 g of an aqueous colloidal silica sol containing 0.4 wt.% of $Na_2O$ and 30.5 wt.% of $SiO_2$. The substance thus obtained has the formula, $5.6K_2O \cdot 5.5Na_2O \cdot Al_2O_3 \cdot 28.5SiO_2 \cdot 463H_2O$.

Then, the reactor was closed tightly, and the substance charged therein was stirred firstly at room temperature for 24 hours and then at 100° C. for 70 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was crystalline zeolite belonging to chabazite group. Also, the elementary analysis showed that the atomic ratio of Si to Al was 3.11 and the copper content was 1.7 wt.%. This substance has the formula, $0.21CuO \cdot 0.35K_2O \cdot 0.44Na_2O \cdot Al_2O_3 \cdot 6.22SiO_2 \cdot 12.53H_2O$.

PRESENT SUBSTANCE (11)

Fifteen grams of sodium aluminate containing 26.3 wt.% of $Na_2O$, 43.2 wt.% of $Al_2O_3$ and 30.5 wt.% of $H_2O$, 23.53 g of sodium hydroxide containing 77.5 wt.% of $Na_2O$ and 14.25 g of potassium hydroxide containing 84.0 wt.% of $K_2O$ were dissolved in 179.95 g of distilled water. This solution was added to 244.95 g of an aqueous colloidal silica sol containing 0.4 wt.% of $Na_2O$ and 30.5 wt.% of $SiO_2$. The substance thus obtained has the formula, $2.0K_2O \cdot 5.9Na_2O \cdot Al_2O_3 \cdot 19.6SiO_2 \cdot 316H_2O$.

Then, the reactor was closed tightly, and the substance charged therein was stirred firstly at room temperature for 24 hours and then at 100° C. for 90 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was crystalline zeolite belonging to chabazite group. The elementary analysis showed that the atomic ratio of Si to Al was 3.59 and the copper content was 2.6 wt.%. This substance has the formula, $0.35CuO \cdot 0.29K_2O \cdot 0.36Na_2O \cdot Al_2O_3 \cdot 7.18SiO_2 \cdot 13.20H_2O$.

REFERENCE SUBSTANCE (a)

14.37 Grams of sodium aluminate containing 26.3 wt.% of $Na_2O$, 43.2 wt.% of $Al_2O_3$ and 30.5 wt.% of $H_2O$ and 14.22 g of sodium hydroxide containing 77.5 wt.% of $Na_2O$ were dissolved in 119.81 g of distilled water. This solution was added to 33.54 g of an aqueous colloidal silica sol containing 0.4 wt.% of $Na_2O$ and 30.5 wt.% of $SiO_2$ with stirring. The substance thus obtained has the formula, $4.0Na_2O \cdot Al_2O_3 \cdot 2.8SiO_2 \cdot 137.4H_2O$.

Then, the reactor was closed tightly, and the substance charged therein was stirred firstly at room temperature for 24 hours and then at 100° C. for 65 hours. Precipitated powdery crystals were collected by filtration under reduced pressure, washed with distilled water until the pH of the washings became from about 8 to about 9 and dried at 120° C. for 16 hours.

Next, to 5 g of these crystals were added 118 ml of a 0.04 M aqueous copper sulfate solution, the pH of the system was adjusted to 6.9 with 10% caustic soda and ion exchange was carried out with stirring at room temperature for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was crystalline zeolite belonging to faujasite group. The elementary analysis showed that the atomic ratio of Si to Al was 1.43 and the copper content was 5.4 wt.%.

The electron microscopic measurement showed that the average particle diameter was 2.0 μm. This substance has the formula, $0.38CuO \cdot 0.62Na_2O \cdot Al_2O_3 \cdot 2.8\text{-}6SiO_2 \cdot 6.08H_2O$.

Reference Substance (b)

A zeolite, a precursor, was obtained in the same manner as in the preparation of the reference substance (a). To 5 g of the zeolite thus obtained were added 60 ml of a 0.16 M aqueous copper sulfate solution, the pH of the system was adjusted to 6.9 with 10% caustic soda and ion exchange was carried out with stirring at room temperature for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was crystalline zeolite belonging to faujasite group. The elementary analysis showed that the atomic ratio of Si to Al was 1.43 and the copper content was 9.9 wt.%.

The electron microscopic measurement showed that the average particle diameter was 2.0 μm. This substance has the formula, $0.70CuO \cdot 0.30Na_2O \cdot Al_2O_3 \cdot 2.8\text{-}6SiO_2 \cdot 5.52H_2O$.

Reference substance (c)

Fifteen grams of sodium aluminate containing 26.3 wt.% of $Na_2O$, 43.2 wt.% of $Al_2O_3$ and 30.5 wt.% of $H_2O$ and 21.55 g of sodium hydroxide containing 77.5 wt.% of $Na_2O$ were dissolved in 262.93 g of distilled water. This solution was added to 370.66 g of an aqueous sodium silicate solution containing 9.2 wt.% of $Na_2O$ and 29.0 wt.% of $SiO_2$ with stirring. The substance thus obtained has the formula, $13.9Na_2O \cdot Al_2O_3 \cdot 28.2SiO_2 \cdot 470.9H_2O$.

Then, the reactor was closed tightly, and the substance charged therein was stirred firstly at room temperature for 24 hours and then at 100° C. for 24 hours. Precipitated powdery crystals were collected by filtration under reduced pressure, washed with distilled water until the pH of the washings became from about 8 to about 9 and dried at 120° C. for 16 hours.

Next, copper ion exchange was carried out in the same manner as in the preparation of the present substance (1).

The X-ray diffractometry demonstrated that the powdery substance thus obtained was a non-crystalline aluminosilicate. The elementary analysis showed that the atomic ratio of Si to Al was 3.04 and the copper content was 4.7 wt.%. This substance has the formula, $0.53CuO \cdot 0.47Na_2O \cdot Al_2O_3 \cdot 6.08SiO_2 \cdot 9.92H_2O$.

Reference substance (d)

A zeolite, a precursor, was obtained in the same manner as in the preparation of the reference substance (a). To 5 g of the zeolite thus obtained were added 100 ml of a 0.048 M aqueous copper sulfate solution, the pH of the system was adjusted to 4.2 with 10% hydrochloric acid and ion exchange was carried out with stirring at 75° C. for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was a non-crystalline aluminosilicate. The elementary analysis showed that the atomic ratio of Si to Al was 1.43 and the copper content was 5.5 wt.%. The electron microscopic measurement showed that the average particle diameter was 2.0 μm. This substance has the formula, $0.39CuO \cdot 0.61Na_2O \cdot Al_2O_3 \cdot 2.86SiO_2 \cdot 5.94H_2O$.

Reference substance (e)

35.4 Grams of sodium aluminate containing 26.3 wt.% of $Na_2O$, 43.2 wt.% of $Al_2O_3$ and 30.5 wt.% of $H_2O$ and 29.89 g of sodium hydroxide containing 77.5 wt.% of $Na_2O$ were dissolved in 194.2 g of distilled water. This solution was added 62.07 g of an aqueous sodium silicate solution containing 9.2 wt.% of $Na_2O$ and 29.0 wt.% of $SiO_2$ with stirring. The substance thus obtained has the formula, $4.1Na_2O \cdot Al_2O_3 \cdot 2.0SiO_2 \cdot 92.7H_2O$.

Then, the reactor was closed tightly, and the substance charged therein was stirred firstly at room temperature for 3 hours and then at 60° C. for 3 hours. Precipitated powdery crystals were collected by filtration under reduced pressure, washed with distilled water until the pH of the washings became from about 8 to about 9 and dried at 120° C. for 16 hours.

Next, to 5 g of these crystals were added 60 ml of a 0.16 M aqueous copper nitrate solution, the pH of the system was adjusted to 6.9 with 10% caustic soda and ion exchange was carried out with stirring at room temperature for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was crystalline zeolite belonging to faujasite group. The elementary analysis showed that the atomic ratio of Si to Al was 1.15 and the copper content was 10 wt.%.

The electron microscopic measurement showed that the average particle diameter was 1.8 μm. This substance has the formula, $0.63CuO \cdot 0.37Na_2O \cdot Al_2O_3 \cdot 2.30SiO_2 \cdot 4.91H_2O$.

Reference substance (f)

A zeolite, a precursor, was obtained in the same manner as in the preparation of the reference substance (e). To 5 g of the zeolite thus obtained were added 100 ml of a 0.048 M aqueous copper sulfate solution, the pH of the system was adjusted to 4.2 with 10% hydrochloric acid and ion exchange was carried out with stirring at 75° C. for 4 hours. After the ion exchange had been completed, the reaction solution was filtered, and the resulting crystals were washed with distilled water until copper ions and sulfate radicals were not detectable and dried at 120° C. for 16 hours.

The X-ray diffractometry demonstrated that the powdery substance thus obtained was a non-crystalline aluminosilicate. The elementary analysis showed that the atomic ratio of Si to Al was 1.15 and the copper content was 5.7 wt.%. The electron microscopic measurement showed that the average particle diameter was 1.8 μm. This substance has the formula, $0.36CuO \cdot 0.64Na_2O \cdot Al_2O_3 \cdot 2.30SiO_2 \cdot 5.26H_2O$.

Reference substance (g)

Fifteen grams of sodium aluminate containing 26.3 wt.% of $Na_2O$, 43.2 wt.% of $Al_2O_3$ and 30.5 wt.% of $H_2O$ and 58.48 g of sodium hydroxide containing 77.5 wt.% of $Na_2O$ were dissolved in 374.33 g of distilled water. This solution was added to 249.84 g of an aqueous colloidal silica sol containing 0.4 wt.% of $Na_2O$ and 30.5 wt.% of $SiO_2$ with stirring. The substance thus obtained has the formula, $12.2Na_2O \cdot Al_2O_3 \cdot 20.0SiO_2 \cdot 496H_2O$.

Then, the reactor was closed tightly, and the substance charged therein was stirred firstly at room temperature for 24 hours and then at 100° C. for 24 hours. Precipitated powdery crystals were collected by filtration under reduced pressure, washed with distilled water until the pH of the washings became from about 8 to about 9 and dried at 120° C. for 16 hours.

Next, to 5 g of these crystals were added 118 ml of a 0.5 M aqueous copper sulfate solution, the pH of the system was adjusted to 4.2 with 10% sulfuric acid and ion exchange was carried out with stirring at 70° C. for 4 hours. After the ion exchange had been completed, the reaction solution was filtered, and the resulting crystals were washed with distilled water until copper ions and sulfate radicals were not detectable and dried at 120° C. for 16 hours. The X-ray diffractometry demonstrated that the powdery substance thus obtained was crystalline zeolite belonging to analcime group. The elementary analysis showed that the atomic ratio of Si to Al was 2.41 and the copper content was 2.0 wt.%. This substance has the formula, $0.20CuO \cdot 0.80Na_2O \cdot Al_2O_3 \cdot 4.82SiO_2 \cdot 10.17H_2O$.

Reference substances (h), (i), (j), (k), (l) and (m)

A zeolite, a precursor, was obtained in the same manner as in the preparation of the present substance (5). This substance was ion-exchanged with each of zinc, tin, iron, nickel, magnesium and cobalt according to the foregoing method for ion-exchanging with copper ion. The amount of each metal to be added to 5 g of the above zeolite powder was as follows: 30 ml of a 0.16 M aqueous zinc nitrate solution for zinc ion, 30 ml of a 0.08 M aqueous stannic chloride solution for tin ion, 30 ml of a 0.18 M aqueous ferric chloride solution for iron ion, 100 ml of a 0.05 M aqueous nickel nitrate solution for nickel ion, 100 ml of a 0.12 M aqueous magnesium nitrate solution for magnesium ion, and 100 ml of a 0.04 M aqueous cobalt nitrate solution for cobalt ion. After each solution had been added to 5 g of zeolite, the pH of the system was adjusted to 4.2 with a 10% aqueous caustic soda solution, and the stirring was carried out at 70° C. for 4 hours. After the ion exchange had been completed, the zeolite powder was filtered off, washed with 200 ml of distilled water and dried at 120° C. for 16 hours. The X-ray diffractometry demonstrated that the resulting each powder was crystalline zeolite belonging to faujasite group. The elementary analysis showed that the atomic ratio of Si to Al of each powder was 2.58.

The following table shows the metal content and composition of each substance thus obtained.

| Test substance | Name of metal used for ion exchange | Metal content (wt. %) | Composition |
| --- | --- | --- | --- |
| (h) | Zinc ($Zn^{2+}$) | 5.6 | $0.55ZnO.0.45Na_2O.Al_2O_3.5.16SiO_2.8.98H_2O$ |
| (i) | Tin ($Sn^{4+}$) | 5.3 | $0.28SnO_2.0.44Na_2O.Al_2O_3.5.16SiO_2.8.22H_2O$ |
| (j) | Iron ($Fe^{3+}$) | 7.2 | $0.33Fe_2O_3.0.1Na_2O.Al_2O_3.5.16SiO_2.5.84H_2O$ |
| (k) | Nickel ($Ni^{2+}$) | 5.4 | $0.59NiO.0.41Na_2O.Al_2O_3.5.16SiO_2.9.16H_2O$ |
| (l) | Magnesium ($Mg^{2+}$) | 2.5 | $0.62MgO.0.38Na_2O.Al_2O_3.5.16SiO_2.7.64H_2O$ |
| (m) | Cobalt ($Co^{2+}$) | 4.7 | $0.50CoO.0.50Na_2O.Al_2O_3.5.16SiO_2.8.43H_2O$ |

In the following examples, the controlling activity was evaluated in six grades described below, 5, 4, 3, 2, 1, 0, according to the condition of disease of test plants at the time of examination, i.e. The degrees of colony and infected area on the leaves, stems, etc. observed with the naked eyes.

5 Neither colony nor infected area is observed.
4 About 10% of colony or infected area is observed.
3 About 30% of colony or infected area is observed.
2 About 50% of colony or infected area is observed.
1 About 70% of colony or infected area is observed.
0 More than about 70% of colony or infected area is observed, there being no difference in the condition of disease between the treated and untreated plots.

EXAMPLE 1 CONTROLLING TEST ON DOWNY MILDEW OF CUCUMBER (*Pseudoperonospora cubensis*) (preventive effect)

Sandy loam was filled in plastic pots, and cucumber was sowed and cultivated into seedlings in the second true leaf stage for 20 days in a greenhouse. The wettable powder of each test substance prepared according to Formulation example 1 was diluted with water to a prescribed concentration and foliar-applied onto the seedlings so that the spray liquor was thoroughly attached to the leaf surface. After spraying, the seedlings were inoculated by spraying the spore suspension of *Pseudoperonospora cubensis*. After inoculation, the seedlings were cultivated firstly at 20° C. under a highly humid condition for 1 day, and then under lighting for 5 days to examine the controlling activity. The results are shown in Table 1.

TABLE 1

| Substance No. | Test substance Application concentration (%) | (Copper concentration (ppm)) | Controlling activity |
| --- | --- | --- | --- |
| (1) | 0.260 | (120) | 4 |
|  | 0.065 | (30) | 4 |
| (2) | 0.316 | (120) | 4 |
|  | 0.079 | (30) | 4 |
| (3) | 0.375 | (120) | 4 |
|  | 0.094 | (30) | 3 |
| (4) | 0.353 | (120) | 4 |
|  | 0.088 | (30) | 3 |
| (5) | 0.255 | (120) | 4 |
|  | 0.064 | (30) | 3 |
| (6) | 0.222 | (120) | 4 |
|  | 0.056 | (30) | 3 |
| (7) | 0.235 | (120) | 4 |
|  | 0.059 | (30) | 3 |
| (8) | 0.154 | (120) | 5 |
|  | 0.038 | (30) | 4 |
| (9) | 0.152 | (120) | 5 |
|  | 0.038 | (30) | 4 |
| (10) | 0.706 | (120) | 4 |
|  | 0.176 | (30) | 3 |
| (11) | 0.462 | (120) | 4 |
|  | 0.115 | (30) | 3 |
| (a) | 0.222 | (120) | 3 |
|  | 0.056 | (30) | 0 |
| (b) | 0.121 | (120) | 3 |
|  | 0.030 | (30) | 1 |
| (c) | 0.255 | (120) | 3 |
|  | 0.064 | (30) | 2 |
| (d) | 0.190 | (120) | 3 |
|  | 0.048 | (30) | 1 |
| (e) | 0.120 | (120) | 2 |
|  | 0.030 | (30) | 0 |
| (f) | 0.211 | (120) | 1 |
|  | 0.053 | (30) | 0 |
| (g) | 0.600 | (120) | 0 |
|  | 0.150 | (30) | 0 |
| (h) | 0.214 | (120) | 1 |
|  | 0.054 | (30) | 0 |
| (i) | 0.226 | (120) | 0 |
|  | 0.057 | (30) | 0 |
| (j) | 0.167 | (120) | 0 |
|  | 0.042 | (30) | 0 |
| (k) | 0.222 | (120) | 2 |
|  | 0.056 | (30) | 0 |
| (l) | 0.480 | (120) | 0 |
|  | 0.120 | (30) | 0 |
| (m) | 0.255 | (120) | 1 |
|  | 0.064 | (30) | 0 |
| (A)*[1] |  | (120) | 0 |
|  |  | (30) | 0 |
| (B)* | (120) | 0 |  |
|  |  | (30) | 0 |

*[1]Basic copper chloride (same applies hereinafter).
*[2]Bordeaux mixture (mixture of copper sulfate and quick lime) (same applies hereinafter).

EXAMPLE 2 CONTROLLING TEST ON LATE BLIGHT OF TOMATO (*Phytophthora infestans*) (preventive effect)

Sandy loam was filled in plastic pots, and tomato (var., Ponteroza) was sowed and cultivated into seedlings in the second to third true leaf stage for 20 days in a greenhouse. The wettable powder of each test substance prepared according to Formulation example 1 was diluted with water to a prescribed concentration and foliar-applied onto the seedlings so that the spray liquor was thoroughly attached to the leaf surface. After spraying, the seedlings were inoculated by spraying the spore suspension of *Phytophthora infestans*. After the inoculation, the seedlings were cultivated firstly at 20° C. under a highly humid condition for 1 day, and then under lighting for 5 days to examine the controlling activity. The results are shown in Table 2.

TABLE 2

| Substance No. | Test substance Application concentration (%) | (Copper concentration (ppm)) | Controlling activity |
|---|---|---|---|
| (1) | 0.260 | (120) | 5 |
| | 0.065 | (30) | 5 |
| (2) | 0.316 | (120) | 5 |
| | 0.079 | (30) | 4 |
| (3) | 0.375 | (120) | 5 |
| | 0.094 | (30) | 5 |
| (4) | 0.353 | (120) | 5 |
| | 0.088 | (30) | 3 |
| (5) | 0.255 | (120) | 5 |
| | 0.064 | (30) | 3 |
| (6) | 0.222 | (120) | 5 |
| | 0.056 | (30) | 3 |
| (7) | 0.235 | (120) | 5 |
| | 0.059 | (30) | 5 |
| (8) | 0.154 | (120) | 5 |
| | 0.038 | (30) | 3 |
| (10) | 0.706 | (120) | 5 |
| | 0.176 | (30) | 4 |
| (11) | 0.462 | (120) | 5 |
| | 0.115 | (30) | 5 |
| (a) | 0.222 | (120) | 3 |
| | 0.056 | (30) | 1 |
| (b) | 0.121 | (120) | 3 |
| | 0.030 | (30) | 1 |
| (c) | 0.255 | (120) | 2 |
| | 0.064 | (30) | 0 |
| (e) | 0.120 | (120) | 2 |
| | 0.030 | (30) | 0 |
| (f) | 0.211 | (120) | 0 |
| | 0.053 | (30) | 0 |
| (g) | 0.600 | (120) | 0 |
| | 0.150 | (30) | 0 |
| (h) | 0.214 | (120) | 0 |
| | 0.054 | (30) | 0 |
| (i) | 0.226 | (120) | 0 |
| | 0.057 | (30) | 0 |
| (j) | 0.167 | (120) | 0 |
| | 0.042 | (30) | 0 |
| (k) | 0.222 | (120) | 0 |
| | 0.056 | (30) | 0 |
| (l) | 0.480 | (120) | 0 |
| | 0.120 | (30) | 0 |
| (m) | 0.255 | (120) | 0 |
| | 0.064 | (30) | 0 |
| (A) | | (120) | 0 |
| | | (30) | 0 |
| (B) | | (120) | 0 |
| | | (30) | 0 |

EXAMPLE 3 CONTROLLING TEST ON ALTERNARIA SPOT OF JAPANESE RADISH (PREVENTIVE EFFECT)

Sandy loam was filled in plastic pots, and Japanese radish (var., 60-nichi daikon) was sowed and cultivated into seedlings in the cotyledonous stage for 6 days in a greenhouse. The wettable powder of each test substance prepared according to Formulation example 1 was diluted with water to a prescribed concentration and foliar-applied onto the seedlings so that the spray liquor was thoroughly attached to the leaf surface. After spraying, the seedlings were inoculated by spraying the spore suspension of the fungi of alternaria spot of Japanese radish. After inoculation, the seedlings were cultivated firstly at 18° C. under a highly humid condition for 1 day, and then under lighting for 3 days to examine the controlling activity. The results are shown in Table 3.

TABLE 3

| Substance No. | Test substance Application concentration (%) | (Copper concentration (ppm)) | Controlling activity |
|---|---|---|---|
| (8) | 0.154 | (120) | 4 |
| | 0.038 | (30) | 3 |
| (9) | 0.152 | (120) | 4 |
| | 0.038 | (30) | 3 |
| (b) | 0.121 | (120) | 4 |
| | 0.030 | (30) | 1 |
| (A) | | (120) | 3 |
| | | (30) | 0 |
| (B) | | (120) | 4 |
| | | (30) | 0 |

EXAMPLE 4 CONTROLLING TEST ON ANGULAR LEAF SPOT OF CUCUMBER (*PSEUDOMONAS LACHRYMANS*) (RESIDUAL EFFECT TEST)

Sandy loam was filled in plastic pots, and cucumber (var., Sagami-hanjiro) was sowed and cultivated into seedlings for 35 days in a greenhouse. The wettable powder of each test substance prepared according to Formulation example 1 was diluted with water to a prescribed concentration and foliar-applied onto the seedlings so that the spray liquor was thoroughly attached to the leaf surface. After spraying, the seedlings were cultivated for 7 days in a greenhouse (20° C. in the daytime and 17° C. in the night) and inoculated by spraying the spore suspension of *Pseudomonas lachrymans*. After inoculation, the seedlings were cultivated firstly under a highly humid condition for about 24 hours, and then under the above greenhouse condition for 10 days to examine the controlling activity. The results are shown in Table 4.

TABLE 4

| Substance No. | Test substance Application concentration (%) | (Copper concentration (ppm)) | Controlling activity |
|---|---|---|---|
| (1) | 0.260 | (120) | 4 |
| | 0.065 | (30) | 4 |
| (3) | 0.375 | (120) | 4 |
| | 0.094 | (30) | 4 |
| (6) | 0.222 | (120) | 4 |
| | 0.056 | (30) | 4 |
| (8) | 0.154 | (120) | 4 |
| | 0.038 | (30) | 4 |
| (11) | 0.462 | (120) | 4 |
| | 0.115 | (30) | 4 |
| (b) | 0.121 | (120) | 3 |
| | 0.030 | (30) | 2 |
| (d) | 0.190 | (120) | 3 |
| | 0.048 | (30) | 1 |
| (e) | 0.120 | (120) | 3 |
| | 0.030 | (30) | 0 |
| (f) | 0.211 | (120) | 2 |
| | 0.053 | (30) | 0 |
| (A) | | (120) | 0 |
| | | (30) | 0 |

EXAMPLE 5 CONTROLLING TEST ON BACTERIAL GRAIN ROT OF RICE (*Pseudomonas glumae*) (preventive effect)

Sandy loam was filled in plastic pots, and rice (var., Kinki No. 33) was sowed and cultivated into seedlings for 70 days in a greenhouse. The wettable powder of each test substance prepared according to Formulation Example 2 was diluted with water to a prescribed concentration and sprayed so that the spray liquor was thoroughly attached to the ears. After spraying, the seedlings were air-dried and inoculated by spraying the spore suspension of *Pseudomonas glumae*. After inoculation, the seedlings were cultivated firstly at 23° C. under a dark and highly humid condition for 1 day, and then under a greenhouse condition (27° C.) for 9 days to examine the controlling activity. The results are shown in Table 5.

TABLE 5

| Substance No. | Test substance Application concentration (%) | (Copper concentration (ppm)) | Controlling activity |
|---|---|---|---|
| (1) | 0.520 | (240) | 4 |
| (3) | 0.750 | (240) | 4 |
| (6) | 0.444 | (240) | 4 |
| (8) | 0.308 | (240) | 4 |
| (11) | 0.924 | (240) | 4 |
| (b) | 0.242 | (240) | 1 |
| (d) | 0.380 | (240) | 1 |
| (e) | 0.240 | (240) | 0 |
| (f) | 0.422 | (240) | 0 |
| (A) | | (240) | 0 |

EXAMPLE 6 CONTROLLING TEST ON ANTHRACNOSE OF CUCUMBER (*Colletotrichum lagenarium*) (preventive effect)

Sandy loam was filled in plastic pots, and cucumber (var., Sagami-hanjiro) was sowed and cultivated into seedlings in the cotyledonous stage for 14 days in a greenhouse. The wettable powder of each test substance prepared according to Formulation example 1 was diluted with water to a prescribed concentration and foliar-applied onto the seedlings so that the spray liquor was thoroughly attached to the leaf surface. After spraying, the seedlings were inoculated by spraying the spore suspension of *Colletotrichum lagenarium*. After inoculation, the seedlings were cultivated firstly at 23° C. under a highly humid condition for 1 day, and then under lighting for 4 days to examine the controlling activity. The results are shown in Table 6.

TABLE 6

| Substance No. | Test substance Application concentration (%) | (Copper concentration (ppm)) | Controlling activity |
|---|---|---|---|
| (1) | 0.260 | (120) | 4 |
|  | 0.065 | (30) | 3 |
| (4) | 0.353 | (120) | 4 |
|  | 0.088 | (30) | 1 |
| (6) | 0.222 | (120) | 4 |
|  | 0.056 | (30) | 2 |
| (8) | 0.154 | (120) | 4 |
|  | 0.038 | (30) | 4 |
| (9) | 0.152 | (120) | 4 |
|  | 0.038 | (30) | 4 |
| (10) | 0.706 | (120) | 4 |
|  | 0.176 | (30) | 2 |
| (b) | 0.121 | (120) | 2 |
|  | 0.030 | (30) | 0 |
| (c) | 0.255 | (120) | 3 |
|  | 0.064 | (30) | 0 |
| (e) | 0.120 | (120) | 1 |
|  | 0.030 | (30) | 0 |
| (f) | 0.211 | (120) | 0 |
|  | 0.053 | (30) | 0 |
| (g) | 0.600 | (120) | 0 |
|  | 0.150 | (30) | 0 |
| (A) |  | (120) | 0 |
|  |  | (30) | 0 |

TABLE 6-continued

| Substance No. | Test substance Application concentration (%) | (Copper concentration (ppm)) | Controlling activity |
|---|---|---|---|
| (B) |  | (120) | 0 |
|  |  | (30) | 0 |

What is claimed is:

1. An agricultural and horticultural fungicide consisting essentially of a fungicidally effective amount of at least one crystalline zeolite selected from the group consisting of faujasite group and phillipsite group represented by the formula $$aCuO \cdot (1-a)M_2O \cdot Al_2O_3 \cdot bSiO_2 o19 \, cH_2O$$

wherein M represents sodium and/or potassium, and a is a number greater than 0 and less than or equal to 1, b is a number greater than 3 and less than or equal to 12, and c is a number greater than or equal to 0 and less than or equal to 20,
together with an inert carrier.

2. A method for controlling plant pathogenic fungi which comprises applying a fungicidally effective amount of at least one crystalline zeolite selected from the group consisting of faujasite group, and phillipsite group represented by the formula, $$aCuO \cdot (1-A)M_2O \cdot Al_2O_3 \cdot bSiO_2 \cdot cH_2O$$

wherein M represents sodium and/or potassium, a is a number greater than 0 and less than or equal to 1,
b is a number greater than 3 and less than or equal to 12,
and c is a number greater than or equal to 0 and less than or equal to 20,
to plant pathogenic fungi.

3. A method for controlling plant pathogenic fungi according to claim 2, which comprises applying a fungicidally effective amount of at least one crystalline zeolite selected from the group consisting of faujasite group and phillipsite group represented by the formula, $$aCuO \cdot (1-a)M_2O \cdot Al_2O_3 \cdot bSiO_2 \cdot cH_2O$$

Wherein M represents sodium and/or potassium, a is a number greater than 0 and less than or equal to 1,
b is a number greater than 3.5 and less than 8, and c is a number greater than or equal to 0 and less than or equal to 20
to plant pathogenic fungi.

4. An agricultural and horticultural fungicidal composition consisting essentially of a fungicidally effective amount of at least one crystalline zeolite selected from the group consisting of faujasite group and phillipsite group represented by the formula, $$aCuO \cdot (1-a)M_2O \cdot Al_2O_3 \cdot bSiO_2 o19 \, cH_2O$$

wherein M represents sodium and/or potassium, and a is a number greater than 0 and less than or equal to 1, b is a number greater than 3 and less than or equal 12 and c is a number greater than or equal to 0 and less than or equal to 20, and
an inert carrier selected from the group consisting of kaoline clay, attapulgite clay, bentonite, terra alba, pyrophillite, talc, diatomaceous earth, calcite, corn stalk powder, walnut shell powder, urea, ammonium sulfate, synthetic hydrated silicon dioxide, calcium lignosulfonate, sodium lauryl sulfate, polyoxyethylene sorbitan monooleate, carboxymethyl cellulose and water.

* * * * *